United States Patent [19]
Patel

[11] Patent Number: 5,481,198
[45] Date of Patent: Jan. 2, 1996

[54] METHOD AND DEVICE FOR MEASURING CORROSION ON A PORTION OF A METALLIC PATH CARRYING AN UNDETERMINED LOAD CURRENT

[75] Inventor: Shashikant G. Patel, Atlanta, Ga.

[73] Assignee: The Georgia Power Company, Atlanta, Ga.

[21] Appl. No.: 296,497

[22] Filed: Aug. 26, 1994

[51] Int. Cl.$^6$ .......................... G01N 27/04; G01R 31/02
[52] U.S. Cl. ...................... 324/700; 324/71.2; 324/541; 324/544; 204/153.11; 204/404
[58] Field of Search .................................. 324/700, 713, 324/715, 718, 71.1, 71.2, 707, 709, 539, 541, 543, 544, 509, 510, 522, 523, 67; 204/404; 7/153.11

[56] References Cited

U.S. PATENT DOCUMENTS

| | | | |
|---|---|---|---|
| 4,019,133 | 4/1977 | Manley et al. | 324/71.2 X |
| 4,048,558 | 9/1977 | Goodman | 324/715 X |
| 4,321,543 | 3/1982 | Vernier . | |
| 4,415,850 | 11/1983 | Sherwood | 324/509 |
| 4,746,241 | 5/1988 | Burbank, III . | |
| 4,839,598 | 6/1989 | Calvert et al. | 324/539 |
| 4,857,830 | 8/1989 | Matsuno | 34/707 |
| 5,101,161 | 3/1992 | Walsh et al. | 324/543 |
| 5,301,121 | 5/1994 | Garverick et al. | 324/483 |
| 5,347,212 | 9/1994 | Bass et al. | 324/544 X |

FOREIGN PATENT DOCUMENTS 2735756  2/1979  Germany .

OTHER PUBLICATIONS

Axsmith, Walter G. and Bass, Craig, Overground Method Locates Concentric–Neutral Corrosion, *Transmission and Distribution*, pp. 26–32 (Jul. 1993).

Baver, Donald K., Overground Method Pinpoints Concentric–Neutral Corrosion, *Transmission and Distribution*, pp. 48–54 (Jul. 1989).

*Primary Examiner*—Kenneth A. Wieder
*Assistant Examiner*—Diep Do
*Attorney, Agent, or Firm*—Needle & Rosenberg

[57] ABSTRACT

A method for determining whether a metallic path (such as a wire) under test carrying an undetermined load current is so corroded as to require replacement applies a test current to the metallic path under test and a total current passing through the metallic path, equal to the sum of the undetermined load current and the test current, is measured. A voltage between two selected points, separated by a known length, on the metallic path is also measured. Resistance of the metallic path is then calculated by measuring an angular phase difference between the voltage and the total current, calculating an impedance of the metallic path from the values of the voltage and the total current then multiplying the impedance by the cosine of the angular phase difference. The resistance of the metallic path under test is correlated to the resistance of metallic paths of known corrosion to determine the degree of corrosion on the metallic path under test. The metallic path is replaced if the degree of corrosion exceeds a predetermined value. The disclosed invention is especially useful in detecting corroded underground neutral wires that run between padmount transformers. An apparatus for measuring corrosion on a wire under test comprises means for supplying an alternating test current to the wire under test, means for measuring a total current flowing through the wire, means for measuring the voltage across the wire under test, and calculating means for determining the amount of corrosion on the wire under test.

24 Claims, 5 Drawing Sheets

5,481,198

METHOD AND DEVICE FOR MEASURING CORROSION ON A PORTION OF A METALLIC PATH CARRYING AN UNDETERMINED LOAD CURRENT

BACKGROUND OF THE INVENTION

1. Field of the Invention

The present invention relates to measuring corrosion on a metallic path, and in particular to a method and apparatus for measuring the corrosion on an exposed underground neutral wire.

2. Description of the Prior Art

Many installations of padmount transformers have cables running between them that include an outer concentric neutral wire wrapped around the insulation that covers the phase conductors. This neutral wire is often a bare wire that is exposed to the earth and is subject to corrosion. Corrosion undesirably increases the resistance of the neutral wire. If the resistance becomes too high, the neutral is unable to provide a safe current return path and the cable must be replaced.

Other phenomena may also cause the neutral resistance to increase, rendering the cable unfit to use. Inadvertent damage during installation or digging and direct lightning strikes can damage the neutral strands, increasing the resistance of the neutral.

Newer installations may have a semiconducting or insulating jacket over the neutral wire to reduce corrosion. However, jacketed neutrals are also subject to damage.

At present, if an electric utility customer complains about voltage and related problems, the standard practice is to replace all suspected underground cables in the area. This practice is costly and time consuming. Furthermore, it often results in the unnecessary replacement of cables having uncorroded neutral wires. A test system that can isolate a corroded neutral wire is therefore desirable.

In residential power distribution applications, disconnecting a neutral wire from a padmount transformer to perform a test on the wire requires the crew member to interrupt the electrical service to the customers receiving power from the padmount. Interrupting electrical service is time consuming, inconvenient and sometimes impossible. Therefore, a neutral wire corrosion tester should have the ability to test for corrosion of the neutral wire without requiring disconnection of the neutral wire from regular service.

Methods of testing underground neutral wire corrosion have been reported in the professional literature. In "Overground Method Pinpoints Concentric-Neutral Corrosion," by Donald K. Baver, P. E., Transmission & Distribution, p. 48, July 1989, a neutral wire corrosion detection method is described in which a high frequency voltage is applied to the neutral wire. The step volate along the surface is measured by conducting an overland survey in which surface voltage is measured at preselected probes placed in the ground. When current meets a resistance in a ground wire, it will seek an alternate path, resulting in a corresponding voltage can be measured at the ground surface. A significant disadvantage of this method, however, is that it requires the application of a non-standard frequency to the neutral and that an overland survey be performed along the entire surface over which the cable runs to detect neutral wire corrosion.

"Underground Method Locates Concentric-Neutral Corrosion," by Walter G. Axsmith, et al., Transmission & Distribution, p. 26, July 1993, describes a method similar to that of the Baver reference, except that the overland survey is conducted by a person fitted with shoe-mounted reference electrodes who walks along the path of the line being measured.

Several devices used to detect the condition of power transmission wires are also known. For example, Vernier, (U.S. Pat. No. 4,321,643), describes a system which detects shorts and opens in ground wires wherein a complete conductive loop is established between a ground conductor and a pilot wire. A sensing signal is coupled onto the loop. Voltage and current in the loop are separately sampled and analysis is performed on these samples to detect any change in resistance. However, the Vernier device does not determine wire resistance, as is necessary for measuring corrosion, but rather detects only shorts and opens in a ground line. Additionally, the neutral wire under test requires isolation from the neutral system consisting of several parallel paths.

Sherwood (U.S. Pat. No. 4,415,850) shows a system that detects shorts and opens in ground wires that comprises power conductors and a pilot wire. An AC test signal is applied to a loop composed of the ground conductor and pilot wire and a terminating impedance and is sampled by a current transformer. However, the Sherwood device does not determine wire resistance, but rather detects only shorts and opens in a ground line.

Burbank, III (U.S. Pat. No. 4,756,241) shows a hinge clamp for securing a sensor module on a power transmission line. The sensor module contains means for sensing various parameters of a power conductor, such as power factor, voltage, frequency, etc. The signals produced by the sensors are converted to digital form and transmitted to a receiver. A zero-crossing detector is used to detect the zero crossings of the current. The Burbank device does not measure resistance, but rather it measures electrical parameters on a transmission line.

Matsuno (U.S. Pat. No. 4,875,830) shows a method for measuring insulation deterioration by measuring resistance of an electric line. It incorporates a phase-correcting device that corrects any phase shift that occurs during resistance measurement. Matsuno measures insulation resistance, and does not measure conductor resistance and, therefore, does not measure corrosion. Furthermore, it does not use line frequency current.

Hauser, et al. (German Patent No. 27 35 756) shows a method for determining earth leakage direction in compensated power networks. It involves phase analysis of voltages and currents of a frequency higher than the power frequency using a reactive idle power relay. It is designed to enable faulty conductor identification. However, it does not measure wire corrosion, and it does not use line frequency current.

Walsh et al. (U.S. Pat. No. 5,101,161) shows a nondestructive energization status tester for electric power cables that uses AC signals and resistance measurements. Carverick, et al. (U.S. Pat. No. 5,301,121) disclose a method for measuring electrical parameters of a power line operation using a digital computer. The system includes analog to digital converters for digitizing the sensor responses. Neither measures corrosion on a wire.

There is thus a need for a neutral wire corrosion tester that will enable a crew member to determine the corrosion on an underground wire without performing an overland survey, so that an objective decision as to replacement of the cable can be made.

There is also a need for a neutral wire corrosion tester that will enable a crew member to determine the corrosion on an underground wire without disconnecting electrical service to the residential customer.

There is also a need for a neutral wire corrosion tester that will enable a crew member to determine the corrosion on an underground wire using current of the same frequency as the standard electrical service frequency.

SUMMARY OF THE INVENTION

The present invention is a method and an apparatus for determining whether a metallic path under test carrying an undetermined load current is so corroded as to require replacement. A metallic path is any metal object capable of carrying a current. The metallic path could comprise an electrical wire (such as an underground neutral wire), a counter poise used for electrical grounding or an electrical power distribution wire. The present invention, however, is not limited to testing electrical paths. In alternative embodiments, it could be used to test such metal paths as: water distribution pipes, metal pipelines, rail lines, fence wires, and even structural beams in buildings. It will be appreciated by one skilled in the art that the present invention could be used to test any metal member capable of acting as a current path.

In a preferred embodiment, a method and apparatus is provided for testing the neutral wire running between power transformers, such as padmount transformers that can be seen in many residential subdivisions, with underground electrical wiring. Such transformers are typically separated by distances of 100 to 900 feet, depending upon residential load requirements and other factors. It should be noted that the inventive method will work for overhead wires and other types of wires as well.

To determine the corrosion on a wire under test, a pre-determined alternating test current is applied to the wire under test. The current can be supplied from either the normal service connection to a padmount transformer or from a portable generator. The current supplied is preferably in the range of 20 to 50 amperes. Use of direct current (DC) or a frequency other than the power frequency may interfere with the customer's load.

The reason for limiting the test current is that if the neutral wire is broken, or for some other reason it has an extremely high resistance, the current injected into the neutral wire under test will seek alternate conduction paths. One such path is through the ground and neutral wiring in the customer's home. Excessive current flowing through these paths could damage the customer's electrical system. Therefore the test current is preferably limited to no more than 50 amps—a safe value. Also, currents less than about 20 amps may not be sufficient in all cases to ensure accurate measurement of current flowing through the wire under test. Thus, a current of 30 amps is preferable in residential applications.

To ensure that the magnitude of the total current is sufficient for accurate measurement, the polarity of the test current is aligned with the polarity of the load current already in existence in the neutral. This ensures that the magnitude of the sum of the load current and test current is greater than the individual magnitudes of the load current and the test current.

A total current, equal to the sum of the undetermined load current and the test current, passing through the wire is measured. A voltage between two selected points, separated by a known length, on the wire under test is also measured. The resistance of the wire under test is then calculated from the values of the total current, the voltage, and the power factor (which is determined from the waveforms of the voltage and the current). Next, the resistance of the wire under test is correlated to the resistance of wires of known corrosion to determine the degree of corrosion on the wire under test.

Calculating the resistance of the wire under test may be done by first determining an angular phase difference between the voltage and the total current. This determination may be done by detecting zero-crossings of the waveforms of the voltage and the total current, determining the time difference between the zero-crossings of the voltage and the total current, and transforming the time difference into a value representative of angular phase difference. Next, the impedance of the wire can be calculated from the values of the voltage and the total current. The resistance of the wire can then be calculated by multiplying the impedance of the wire by the cosine of the angular phase difference. In a preferred embodiment, the resistance per unit length of the wire under test is then calculated by multiplying the resistance of the wire under test by a unit length and dividing the result by the known length.

Correlating the resistance of the wire to the resistance of wires of known corrosion to determine the degree of corrosion can be done using an electronic memory device, e.g., as part of a digital computer, based on input values of the wire type and resistance. The memory device could implement a look-up table in which values of resistance and wire type are used to address corrosion values stored in the electronic memory device.

When the degree of corrosion exceeds a predetermined value, the wire is replaced. One of the criteria may be that if the resistance of the wire under test is greater than 125% of its expected uncorroded value, the cable should be replaced. This threshold could be varied for some applications, if it is appropriate to do so. It should also be noted that the present invention can identify a partially defective cable neutral rather than just a short or an open.

Thus, in a preferred embodiment, the test system comprises: a current supply for injecting a current into the portion of the neutral wire being tested, a voltage sensing unit, a current sensing unit, and a calculating unit that determines the corrosion on the wire based on the values of the voltage, the current, and the power factor.

The current supply comprises a current source, which may be either an electrical service connection to the padmount transformer or a portable generator. It also comprises a current supply cable for connecting the current supply to the neutral wire and a current return cable for connecting the current return to the neutral wire. Current passing through the neutral wire is sensed with a current probe, preferably a clamp-on type that can be clamped around the neutral wire, allowing the test to be performed without disconnecting the neutral.

In the case of padmounts, a test AC current of preferably about 30 amperes, which may be obtained either directly from one of the transformers or from a portable generator, is applied to the neutral wire at one of the padmounts and returned through a cable connected to the neutral wire at an adjacent padmount. The magnitude of the test AC current is selected to be low enough to avoid it entering residential property and disturbing the customer while still providing a sufficiently high enough current for convenient and accurate measurement with a clamp-on probe. It will be understood that the magnitude of the current applied will depend on the application. For residential use, a current in the range of 20 to 50 amperes is satisfactory. Also, while 60 Hz alternating current is convenient and available, the method will work with any other low-frequency alternating current.

The voltage sensing unit employs a first voltage cable and a second voltage cable for connecting the neutral wire to a voltage sensor. The voltage sensor senses the voltage across the neutral wire under test.

The calculating unit, in a preferred embodiment, comprises a microprocessor with a control input, a voltage level input, a current level input, and a data output representative of the corrosion on the neutral wire. The microprocessor calculates the phase difference between the digital voltage signal, the impedance of the neutral wire, the overall resistance of the neutral wire, and the unit resistance of the neutral wire, and generates the data output, which may be the decision whether to replace the neutral wire, based on the unit resistance.

The power factor can be determined by observing the difference between the current and voltage waveforms. An analog to digital converter may be used for this determination. The phase angle θ can be determined by measuring the difference in time between zero crossings of the current waveform and the voltage waveform. The power factor, cos θ, is determined and the unit resistance per 100 feet, $R_{100}$, of the neutral conductor may then be computed employing the formula:

$$R_{100} = \frac{V \times \cos\theta}{I} \times \frac{100'}{L_{neutral}}$$

Where V is the measured voltage across the wire under test, I is the measured current flowing through the wire under test and $L_{neutral}$ is the length of the wire under test.

Thus, the decision regarding the neutral wire can be made based solely upon the resistive component of its impedance. The nominal resistance of the neutral wire for a given length of cable is known or can readily be computed. If the measured resistance is greater than about 125% of the nominal resistance, replacement of the cable is indicated. The replacement criteria can be changed based on the application.

In a preferred embodiment, the test system includes a cable reel mounted with 500 feet of two conductor insulated cable. Placing special connectors at every 100 feet allows unwinding of only the length needed to reach between the transformers. If more than 500 feet of cable is needed, two or more of these reels can be easily connected in series.

Under normal circumstances, a current carrying lead must be separated from the voltage measuring lead to minimize the inductive coupling and resulting error in the voltage measuring circuit. Because this method distinguishes and measures the resistive component of the impedance of the neutral under test, the measured resistance remains unaffected even when both the leads are enclosed in a single cable, regardless of cable length. Thus it is possible to use only one cable reel.

The invention has the advantage of avoiding the use of DC to determine the neutral resistance. DC would go through the transformer and into the customer's house and would make it more difficult to measure current with a clamp-on meter. Testing of a neutral while the neutral remains in service is also possible, even when the wire under test carries a customer's load current. The present invention also avoids using higher frequency current, as higher frequency current has adverse effects on customers' loads.

In addition to determining the neutral resistance, the inventive test method can, possibly with additional instruments or computations, measure impedance (resistance and inductance) of the neutral under test, measure impedance (resistance and inductance) of the entire neutral system connected between the two transformers (allowing for evaluation of electric substation ground grids), and determine heavily corroded or broken spots on the neutral by surveying 60 Hz voltage gradients on the surface of the earth above the neutral.

It is, therefore, an object of this invention to provide a neutral wire corrosion tester that enables determination of the corrosion on an underground wire without performing an overland survey.

It is a further object of the present invention to provide a neutral wire corrosion tester that determines corrosion that is less advanced than that which can be measured by the overland survey method.

It is a further object of this invention to provide a neutral wire corrosion tester that enables determination of the corrosion on an underground wire without disconnecting electrical service to the residential customer.

It is a further object of this invention to provide a neutral wire corrosion tester that enables determination of the corrosion of an underground wire using current of the same frequency as the standard electrical service frequency.

These and other objects will become apparent from the following description of the preferred embodiment taken in conjunction with the following drawings, although variations and modifications may be effected without departing from the spirit and scope of the novel concepts of the disclosure.

DETAILED DESCRIPTION OF THE INVENTION

Figure 1:
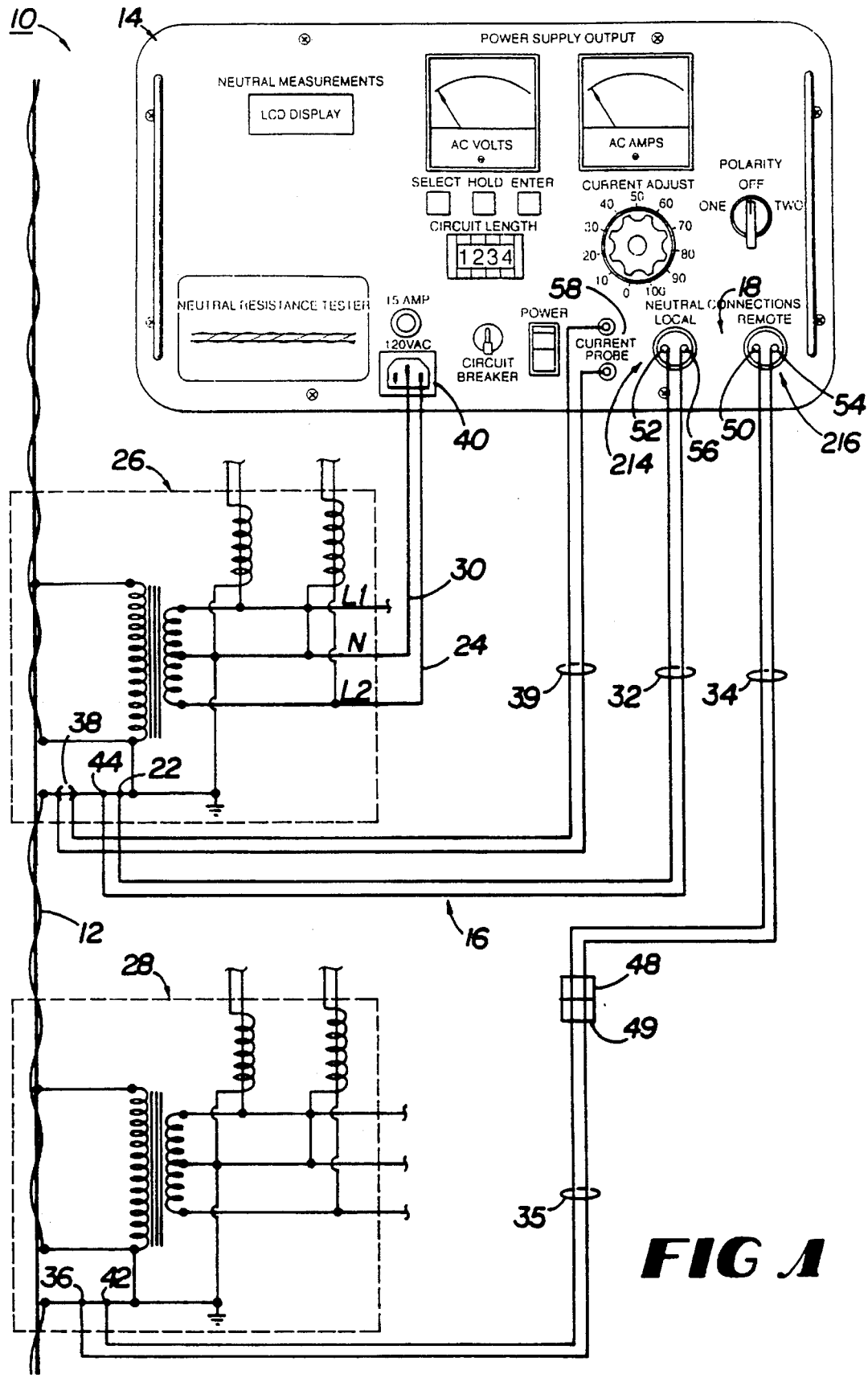
FIG. 1 is a schematic view of the present invention operationally connected to a neutral wire running between two padmount transformers.

A preferred embodiment of the invention is now described in detail. Referring to the drawings, like numbers indicate like parts throughout the views. In the following discussion and the claims that follow, it is to be understood that the parameters "current" and "voltage" are used to describe AC values. Both &these parameters refer to a waveform, having a magnitude component and a phase component. When it would be obvious to one skilled in the art, reference will be made to these parameters in a way that refers to only one of the components of the parameter. Also, these parameters will refer to DC values when describing logic and associated electronic components, following normal usage in the art.

As shown in FIG. 1, the present invention 10, designed to test a metal path comprising an exposed underground neutral wire, is an apparatus for determining the amount of corrosion on a wire under test 12. Typically, the wire under test 12 will be an underground neutral wire running from a first padmount transformer 26 to a second padmount transformer 28. The wire 12 will usually carry an undetermined load current, representing the return current from the installations being serviced by the padmount transformer 26. An instrument enclosure 14 houses a connection to a power supply 40, which could comprise a connection to the power supply 24 and power return 30 of a padmount transformer 26 or a connection to the power supply and return of a portable generator (not shown).

Connecting the instrument enclosure 14 to the wire under test 12 is a local cable 32 and a remote cable 14. Both of these cables comprise two wires. The local cable 32 has a wire connecting a first supply point 22 on the wire under test 12 to a local cable connector 214 on the instrument enclosure 14 and a voltage sensing wire connecting a first potential-sensing point 44 on the wire under test 12 to the local cable connector 214.

The remote cable 34 has a current supply wire connecting a second supply point 36 on the wire under test 12 to a remote cable connector 216 on the instrument enclosure 14 and a wire connecting a second potential-sensing point 42 on the wire under test 12 to the remote cable connector 216. The voltage sensing terminals 54, 56 are connected to means for measuring voltage 18 housed inside the enclosure 14. The current supply terminals 50, 52 supply a test current to the wire 12.

The first potential-sensing point 44 and the second potential-sensing point 42 cannot lie outside of the first supply point 22 and the second supply point 36, thereby ensuring that the voltage sensed corresponds to the total current flowing through the wire under test 12. The total current includes both the test current and the load current. In one preferred embodiment, the first potential-sensing point 44 and the first supply point 22 are at the same point on the wire under test 12 and, likewise, the second potential-sensing point 42 and the first supply point 36 are at the same point on the wire under test 12.

The current measuring means 16 comprises a wire 39 connecting a current-sensing clamp-on probe 38 to a current sensing terminal 58 housed in the enclosure 14. The probe 38 is capable of being clamped around the wire under test 12 and generating a signal representative of the total current passing through the wire 12 near the point where the probe 38 is clamped on. The current measuring means 16 could also comprise a clamp-on ammeter (not shown) used in the same manner as the probe 38. The current probe 38 is clamped onto the wire 12 between the first potential-sensing point 44 and the second potential sensing point 42 to ensure that the current measured corresponds to the voltage measured by the voltage sensing means 18. By measuring the total current passing through the wire 12, and the resulting voltage, the operator is able to test the corrosion on the wire 12 without having to disconnect it from normal service. This is because the total current comprises any current flowing through the wire 12 as a result of normal service added to the test current and the voltage measured by the voltage sensing means 18 is the voltage induced by the total current, not merely the test current.

Figure 2:
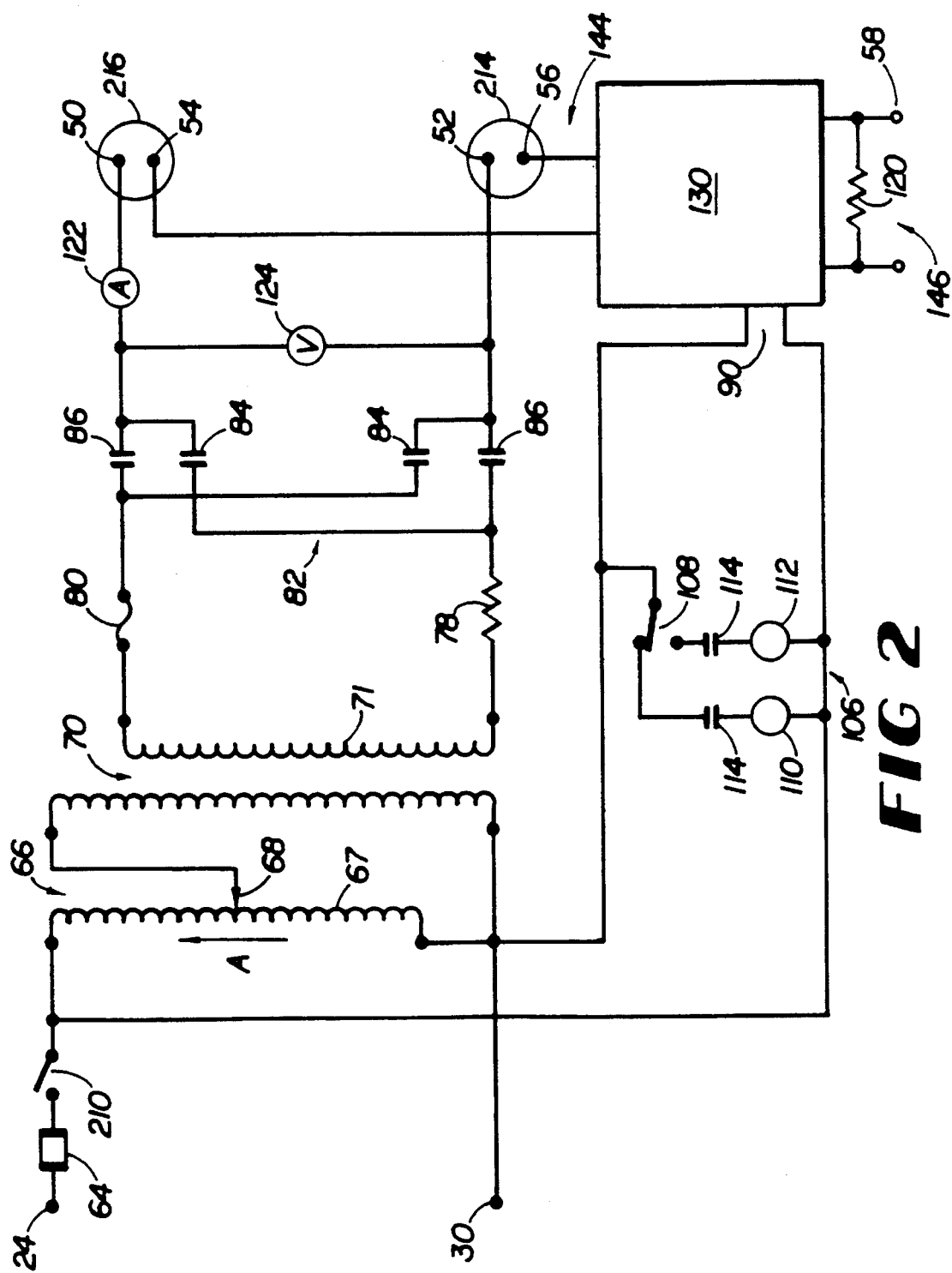
FIG. 2 is a schematic view of the electrical components of the power supply and sensing circuits of the present invention.

As shown in FIG. 2, the electrical components of the power supply and sensing circuits comprise a power supply connection 24 to a power supply (such as a padmount transformer or a portable generator) and a power return connection 30. A fuse 64 protects the system from current surges and a power switch 210 can isolate the system from the power supply.

A variable transformer 66, comprising a primary winding 67 and a contact 68, controls the amount of test current passing through the system. By changing the position of the contact 68 relative to the primary winding 67, the operator can adjust the current from zero amperes to a predetermined maximum (such as 50 amperes, as used in one preferred embodiment). As the contact 68 is moved in the direction of arrow A, the current flowing through the primary winding 67 increases.

The current next flows through a power transformer 70 having a secondary winding 71. Test current from one side of the secondary winding 71 flows through a buffering resistor 78 which limits current in case of shorts in the system. On the other side of the power transformer 70 the test current flows through a circuit breaker 80, which can open the circuit supplying the test current if the test current exceeds a predetermined value.

The test current then flows through a polarity alignment circuit 82. The polarity alignment circuit 82 aligns the polarity of the test current to the polarity of the load current on the wire under test 12. This is done so that the magnitude of the total current is additive. In other words, the polarity alignment circuit 82 ensures that the magnitude of the total current is greater than the individual magnitudes of the load current and the test current.

The polarity alignment circuit 82 comprises two first polarity contactors 84 and two second polarity contactors 86. If the first polarity contactors 84 are closed then the second polarity contactors 86 are open and the test current will have a first polarity. If the second polarity contactors 86 are closed then the first polarity contactors 86 are open and the test current will have a second, opposite, polarity. If both sets of polarity contactors 84, 86 are open then no test current flows through the system.

The polarity contactors 84, 86 are activated by the polarity control unit 106. The polarity control unit 106 comprises a polarity select switch 108, a first contactor power supply 110 that activates the first polarity contactors 84 and a second contactor power supply 112 that activates the second polarity contactors 86. The polarity select switch 108 connects power supply 24 to the first contactor power supply 110, to the second contactor power supply 112, or to neither power supply (in which case, both sets of polarity contactors 84, 86 are open and no test current flows through the system). Current flowing through power supplies 110, 112 also flows through auxiliary contactors 114 (usually closed) and to the power return 30. From the polarity alignment circuit 82, the current is measured by a current meter 122 and a volt meter 124 for display to the operator. The current then flows to the test current supply terminal 50 and return terminal 52.

Also shown in FIG. 2 is the electronics unit 130. The electronics unit 130 has a power supply connection 90 to the power switch 210 and power return 30 to provide operating power. The electronics unit 130 has an input from the remote voltage sensing terminal 54 and the local voltage sensing terminal 56. The current sensing terminal 58 provides the electronics unit 130 with a current level input, across a resistor 120.

Figure 3:
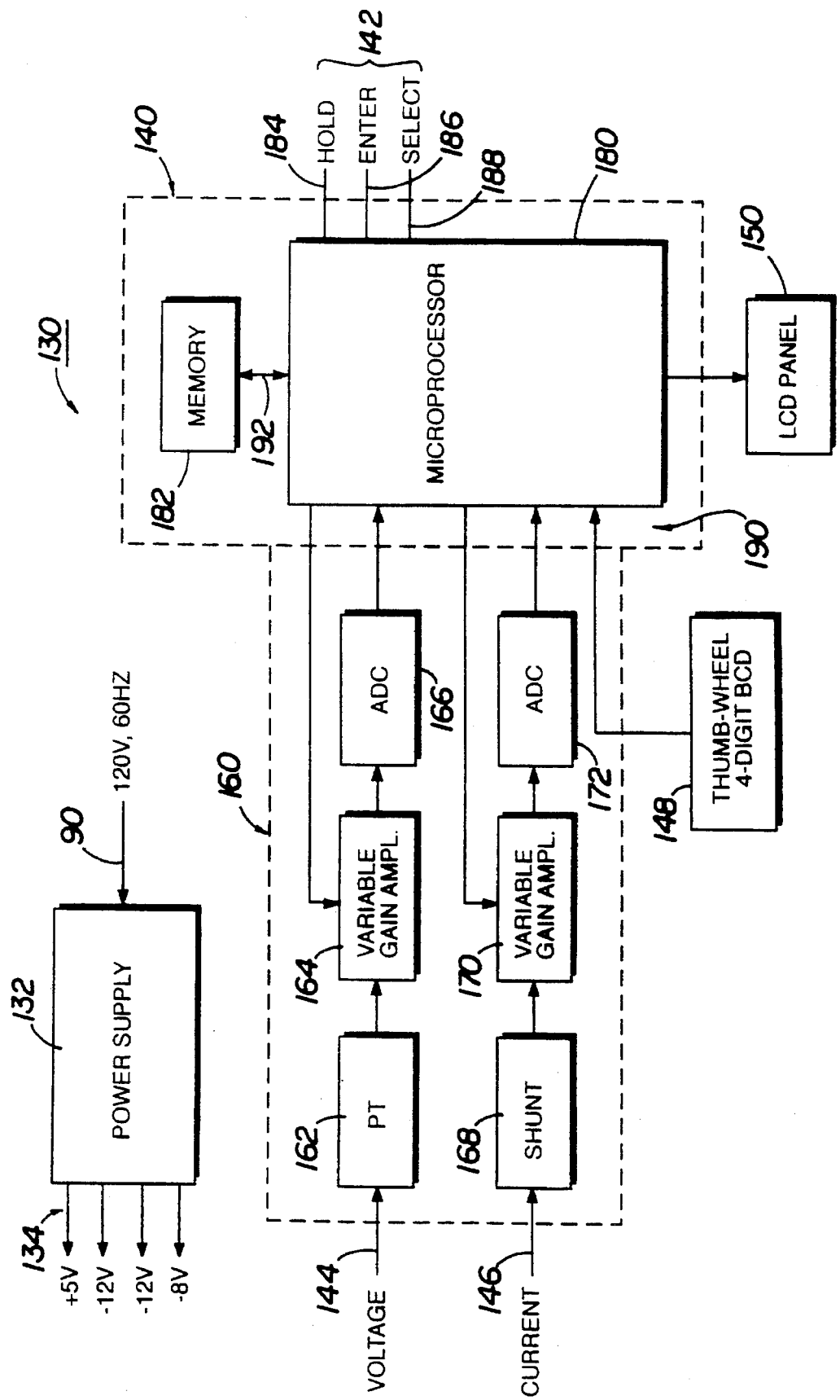
FIG. 3 is a block diagram of the sensing and calculating electronics unit of the present invention.

The electronics unit 130 is shown in more detail in FIG. 3. It comprises a power supply 132 which transforms AC power from the power supply input 90 into DC levels 134 usable by the components in the electronics unit 130. These levels typically include +5 V, +12 V, −12 V, −8 V, depending on the logic families of the components used. The electronics unit 130 also comprises a calculating unit 140, a signal conditioning unit 160, a sensed voltage input 144, a sensed current probe input 146, a control input 142, a cable length input 148 and a display output 150.

The signal conditioning unit 160 takes the sensed voltage input 144 and the sensed current probe input 146 and translates them into digital signals receivable by the calculating unit 140. The current from the voltage input 144 first passes through a potential transformer (PT) 162. The potential transformer 162 is an isolation transformer that preserves the voltage of the signal. The signal from the potential transformer 162 is received by a voltage signal amplifier 164 which amplifies the signal as required by an analog-to-digital converter (ADC) 166 to achieve maximum accuracy. The amplifier gain is automatically controlled by the control signal 190 from the calculating unit 140. That signal is transformed by ADC 166 into a digital signal representative of voltage, the digital signal receivable by the calculating unit 140.

The signal from the current probe input 146 is a current signal which passes through a resistive shunt 168 that transforms the current signal into a voltage signal with a relatively wider range. The resistance of the resistor determines the range of the voltage signal. For example, if the maximum value of the current signal were to be 5 mA and a 5 ohm resistor were used for the shunt 168, then the range of the resulting voltage signal across the shunt 168 would be 0 mV to 25 mV. The voltage signal from the shunt 168 is received by a voltage signal amplifier 170 which amplifies the signal as required by an ADC 172. The amplifier gain is automatically controlled by a control signal from the calculating unit 180. That signal is transformed by ADC 172 into a digital signal representative of current, which is receivable by the calculating unit 140.

The signal amplifiers 164, 170 are automatic gain controlled to accommodate extreme signal ranges. They also contain filter circuits to maintain signal purity and improve accuracy.

The calculating unit 140 comprises a microprocessor 180 connected to a memory 182 by a memory bus 192. The microprocessor 180 is connected to a data bus 190 which provides a voltage level input from ADC 166, a current level input from ADC 172 and a data output to the display 150. The memory 182 holds signal characterization data, program data, and a wire corrosion look-up table.

The calculating unit 140 determines the corrosion on the wire under test 12 by using the digital voltage signal from ADC 166 and the digital current signal from ADC 172 to calculate the resistance of the wire 12. To do this it analyzes the current and the voltage waveforms, calculating the phase angle θ, which is determined by measuring the difference in time between zero crossings of the current waveform and the voltage waveform. Once the phase angle, θ, has been determined from the zero crossings of the current waveform and the voltage waveform, using methods well known to the art, the power factor is then calculated. The power factor is equal to the cosine of the phase angle, cos θ. The unit resistance per 100 feet, $R_{100}$, of the neutral conductor is then computed employing the following formula:

$$R_{100} = \frac{V \times \cos\theta}{I} \times \frac{100'}{L_{neutral}}$$

where V is the measured voltage across the wire under test, I is the measured current flowing through the wire under test, and $L_{neutral}$ is the length of the wire under test.

The use of this equation allows resistance to be obtained by removing the reactance component from the impedance (given by V/I when using alternating current) by multiplying the impedance by the power factor. Therefore, the decision to replace or not to replace the neutral wire can be based solely upon the resistive component of its impedance, eliminating the effect of reactive coupling in either the wire under test 12 or the cables 32, 34. The nominal resistance of the neutral wire for a given length of cable is stored in a look-up table in the memory 182 or is otherwise known or readily computed. If the measured resistance is greater than about 125% of the nominal resistance, replacement of the cable is indicated.

Control inputs 142 to the microprocessor 180 allow the operator to perform tests and display the results. The enter button 186 allows the operator to enter cable length via the cable length input 148 which may comprise a binary-coded-decimal (BCD) rotary thumbwheel switch. The hold button 184 acts as a trigger and causes the microprocessor 180 to capture the voltage and current values at a particular moment. The select button 188 allows the operator to select a desired parameter (such as sensed voltage, sensed current, power factor, resistance etc.) for the microprocessor 180 to output to the display 150. In one preferred embodiment the display 150 comprises a liquid-crystal display. Selection of the particular microprocessor and display would depend on the desired features of a particular embodiment, the criteria being well known to those skilled in the art.

Figure 4:
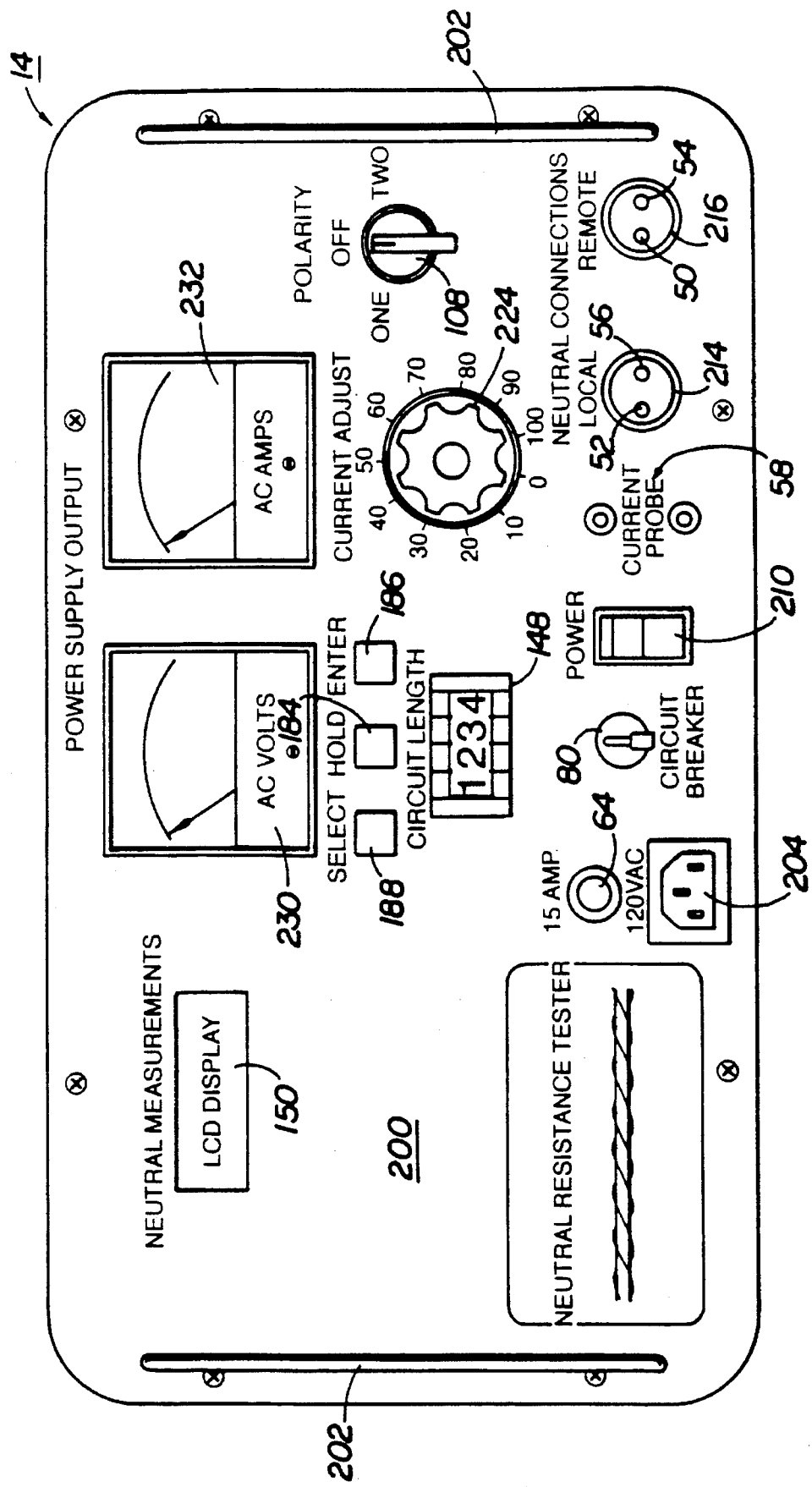
FIG. 4 is a plan view of the front panel of the instrument enclosure of the present invention.

The front panel 200 of the instrument enclosure 14 is shown in FIG. 4. It has a power supply input plug 204 to receive power from the power supply and a power switch 210 to energize and de-energize the system. The front panel 200 also has a test current level control knob 224 connected to the variable transformer (item 66 in FIG. 2) to allow the operator to adjust the magnitude of the test current. The test current voltmeter 230 and a test current ammeter 232 allow the operator to monitor the actual test voltage and current being applied to the wire under test 12.

The local cable connector 214 connects test current supply terminal 52 and the local voltage sensing terminal 56 to the local cable (item 32 in FIG. 1). The remote connector 216 connects test current supply terminal 50 and the remote voltage sensing terminal 54 to the remote cable (item 35 in FIG. 1). Protective handles 202 are provided on either side of the from panel 200 to provide a gripping surface and to protect the panel instruments from accidental impact.

As shown in FIGS. 5a–5d, the remote cable 234 is stored on a cable reel 46 when not in use. The cable reel 46 holds a plurality of connected sections of cable 234. Each section is of a fixed length, with a female connector 48 at one end and a male connector 49 at the opposite end. To connect the cable, the operator unwinds only the number of sections 34 as needed from the reel 46, disconnects those sections 34 from the reel and connects the exposed male connector 48 to the remote terminal 216 on the enclosure 14.

A test lead 35, having a male connector 49 at one end, is then connected to the exposed female connector 48 of the cable 34, with the other end of the test lead 35 being connected to the wire under test (item 12 in FIG. 1) by a clamp 250. The clamp 250 is electrically connected to both the test current supply wire in the test lead 35 and the voltage sensing wire in the test lead 35. (As the wires reside inside the cable 34 and the test lead 35, they are not shown.) A similar test lead is used to connect the local terminal (item 214 in FIG. 1) to the wire under test (item 12 in FIG. 1). The wire 39 for connecting the current probe (item 38 in FIG. 1) to the current sensing terminal (item 58 in FIG. 1) has a pair of plugs 252 receivable by the probe and the terminal, as shown in FIG. 5d.

Figure 5A:
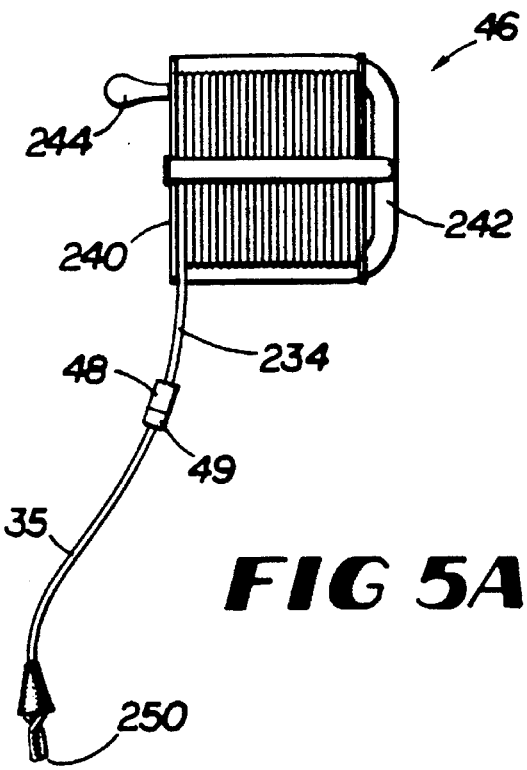
FIG. 5a is a top elevational view of the cable reel with connected sections of remote cable wound around it and a test lead attached to the end of the cable.
Figure 5B:
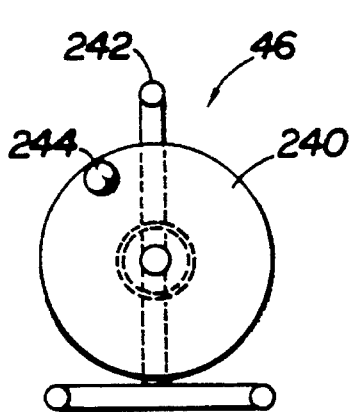
FIG. 5b is an orthogonal projection of side view of an empty cable reel.
Figure 5C:
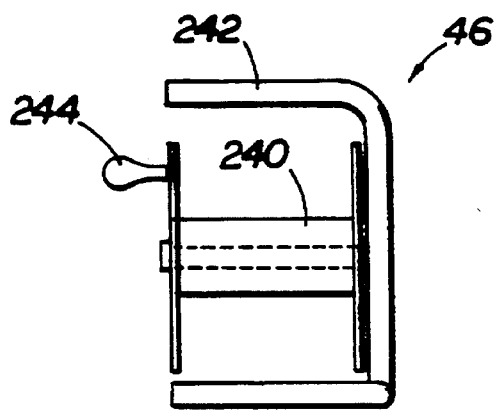
FIG. 5c is an orthogonal projection of front view of an empty cable reel.
Figure 5D:
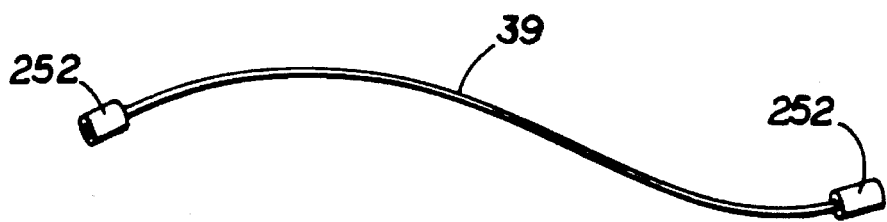
FIG. 5d is a plan view of a wire used to connect the current probe to the instrument module.

As shown in FIGS. 5a, 5b and 5c, the cable reel 46 comprises a spool 240 mounted on a light-weight frame 242. A handle 244 is attached to the spool 240 to facilitate rapid winding and unwinding of the cable 234.

An experimental test of the present invention rendered the following resistance measurements, which are typical:

TABLE 1

| Test | Number of Strands | Span | I | V | PF | $R_n/R_{ref}$ |
|---|---|---|---|---|---|---|
| 1. | 14 | 250 | 19.50 | 2.1 | 0.58 | 1.04 |
| 2. | 14 | 610 | 5.35 | 4.4 | 0.88 | 4.94 |
| 3. | 14 | 115 | 14.00 | 4.3 | 0.81 | 9.01 |
| 4. | 8 | 690 | 0.73 | 5.5 | 0.48 | 12.48 |
| 5. | 8 | 241 | 0.80 | 43.8 | 0.84 | 455.00 |

Where:
Number of strands = the number of strands of wire comprising the neutral wire under test (all strands tested comprised 14 gauge wire)
Span = the length of the neutral span tested in feet.
I = measured total current in the neutral wire under test in amperes
V = the measured voltage in volts
PF = the measured power factor
$R_n/R_{ref}$ = the ratio of the resistance of the neutral wire under test to the resistance of an uncorroded neutral.

From these results, it is estimated that the described embodiment of the present invention will save a typical power company (in 1994 dollars) $22.50 per foot of tested neutral wire as a result of being able to delay the replacement of cables having uncorroded neutral wires. This figure is based on the current practice of most power companies of abandoning any cables suspected of having corroded neutral wires and replacing the abandoned cables with new cables.

The above describe embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A method of determining whether a portion of a metallic path under test carrying an undetermined load current is so corroded as to require replacement, comprising:
   a. applying a pre-determined alternating test current to the portion of the metallic path under test between two selected points separated by a known length, said two selected points being chosen so that they are disposed on the portion of the metallic path under test;
   b. measuring a total current with a current sensing probe applied to the portion of the metallic path under test said total current being equal to the sum of the undetermined load current and the test current passing through the metallic path under test;
   c. measuring a voltage between the two selected points on the metallic path under test;
   d. calculating the resistance of the portion of the metallic path under test between the two selected points from the values of the total current and the voltage; and
   e. correlating the resistance of the portion of the metallic path under test between the two selected points to the resistance of metallic paths of known corrosion to determine the degree of corrosion on the metallic path under test.

2. The method of claim 1 further comprising the step of replacing the metallic path under test when the degree of corrosion exceeds a predetermined value.

3. The method of claim 1 further comprising the step of aligning the polarity of the test current with the polarity of the load current in the metallic path under test so that the magnitude of said total current is greater than the individual magnitudes of the load current and the test current, thereby increasing the accuracy of said current voltage measuring steps.

4. The method of claim 1 wherein the step of calculating the resistance of the metallic path under test comprises:
   a. measuring an angular phase difference between said voltage and said total current;
   b. calculating an impedance of the metallic path under test from the values of the voltage and the total current; and
   c. calculating a resistance of the metallic path under test by multiplying the impedance by the cosine of the angular phase difference.

5. The method of claim 4 wherein the step of measuring angular phase difference between said voltage and said total current comprises the steps of:
   a. detecting zero-crossings of the voltage across two points;
   b. detecting zero-crossings of the total current;
   c. determining the time difference between the zero-crossings of the voltage and the zero-crossings of the total current; and
   d. transforming the time difference into a value representative of angular phase difference.

6. The method of claim 4 further comprising calculating a resistance per unit length of the metallic path under test by multiplying the resistance of the metallic path under test by a unit length and dividing the result by the known length.

7. The method of claim 1 wherein the step of correlating the resistance of the metallic path under test to the resistance of metallic paths of known corrosion to determine the degree of corrosion in the metallic path under test comprises retrieving data from an electronic memory device based on input values comprising metallic path type and resistance.

8. The method of claim 7 further comprising the step of addressing corrosion values stored in an electronic memory device with values of resistance and metallic path type.

9. The method of claim 1 further comprising the step of indicating when the corrosion of the metallic path under test exceeds a predetermined value.

10. A device for measuring corrosion on a portion of a metallic path under test having an undetermined load current passing through it, the device comprising:
    a. means for supplying an alternating test current to the metallic path under test;
    b. means for measuring a total current and for generating a signal representative of said total current, said total current flowing through the portion of the metallic path under test and being equal to the sum of the test current supplied by said supplying means and the load current;
    c. means for measuring the voltage across two preselected points on the metallic path under test through which the total current is flowing and for generating a signal representative of said voltage, said two preselected points being chosen so that the portion of the metallic path being measured lies therebetween; and d. calculating means, responsive to said total current signal and said voltage signal, for calculating the resistance of the portion of the metallic path under test from said total current signal and said voltage signal thereby determining the amount of corrosion on the metallic path under test.

11. The device of claim 10 wherein the calculating means comprises:

a. means responsive to said total current signal and said voltage signal for generating a signal representative of the angular phase difference between the total current and the voltage;

b. means responsive to said total current signal, said voltage signal and said phase difference signal for generating a signal representative of the resistance of the metallic path under test; and c. means responsive to said resistance signal for correlating the resistance of the metallic path under test with the resistances of metallic paths having known mounts of corrosion.

12. The device of claim 10 wherein the supply means comprises a cable connecting a first supply point on the metallic path under test to a service power supply of a padmount transformer and a cable connecting a second supply point on the metallic path under test to a service power return of the padmount transformer.

13. The device of claim 10 wherein the supply means comprises a cable connecting a first supply point on the metallic path under test to a service power supply of a portable generator and a cable connecting a second supply point on the metallic path under test to a service power return of the portable generator.

14. The device of claim 10 wherein the current measuring means comprises:

a. a clamp-on current probe, for clamping around the metallic path under test between the first supply point and the second supply point, and for generating an analog signal representative of the mount of current flowing through the metallic path under test near the point where the probe is clamped around the metallic path; and b. means for translating said analog signal into a digital signal receivable by said calculating means.

15. The device of claim 10 wherein the current measuring means comprises a digital clamp-on ammeter for clamping around the metallic path under test between the first supply point and the second supply point and for generating a signal representative of the current passing through the metallic path near the point where the ammeter is clamped around the metallic path.

16. The device of claim 10 wherein voltage measuring means comprises:

a. means for sensing the voltage between a first potential-sensing point and a second potential-sensing point on the metallic path under test, the first potential-sensing point and the second potential-sensing point both being between the first supply point and the second supply point, and for generating a signal representative of said voltage; and b. means responsive to said voltage signal for translating the voltage sensed into a digital signal receivable by said calculating means.

17. A device for measuring corrosion on a portion of a neutral wire, between a first point and a second point on the neutral wire, carrying an undetermined load current, comprising:

a. a current supply for injecting a test current into the portion of the neutral wire;

b. a voltage sensing unit for sensing the voltage between a first potential-sensing point and a second potential-sensing point on the neutral wire, the portion of the wire being tested defined by the portion between the first sensing point and the second sensing point, and for generating a digital signal representative of said voltage;

c. a current sensing unit for sensing a total current flowing between the first potential-sensing point and the second potential-sensing point, said total current comprising said test current and the undetermined load current, and for generating a digital signal representative of said current; and d. a calculating unit, which receives said digital voltage signal and said digital current signal, for calculating the resistance of the portion of the wire based on the values of the voltage and the current, thereby determining the corrosion on the portion of the wire.

18. The device of claim 17 wherein the current supply comprises:

a. a current source, having a current supply and a current return, for injecting a current flowing between the current supply and the current return;

b. a current supply cable, for electrically connecting the current supply to the first point on the neutral wire; and c. a current return cable, for electrically connecting the current return to the second point on the neutral wire.

19. The device of claim 17 wherein the voltage sensing unit comprises:

a. a first voltage cable, having a proximal end and a distal end, the distal end for electrical connection to the first sensing point on the neutral wire;

b. a second voltage cable, having a proximal end and a distal, the distal end for electrical connection to the second sensing point on the neutral wire; and c. a voltage sensor, electrically connectable to the proximal ends of the first and second voltage cables, for sensing the voltage between the first sensing point and the second sensing point and for generating an analog signal representative of said voltage.

20. The device of claim 19 further comprising a voltage signal conditioner responsive to said analog voltage signal for generating said digital signal representative of said voltage.

21. The device of claim 17 wherein the current sensing unit comprises a current probe, capable of being clamped around the neutral wire at a clamp-on point between the first sensing point and the second sensing point, which produces an analog signal representative of the current passing through the neutral wire at the clamp-on point.

22. The device of claim 21 further comprising a current signal conditioner responsive to said analog current signal for generating said digital signal representative of said current.

23. The device of claim 17 wherein the calculating unit comprises:

a. a microprocessor;

b. a control input to the microprocessor; and c. a data bus which provides a voltage level input to the microprocessor responsive to said digital voltage signal, a current level input to the microprocessor responsive to said digital current signal, and a data output from the microprocessor representative of the corrosion on the neutral wire.

24. The device of claim 17 wherein the calculating unit comprises:

a. means for calculating the phase difference between the digital voltage signal and the digital current signal by detecting zero-crossings of the digital voltage signal and the digital current signal, determining a time difference between said zero-crossings, and transforming said time difference into a corresponding angular phase difference;

b. means for calculating the impedance of the neutral wire by dividing the magnitude of the digital voltage signal by the magnitude of the digital current signal;

c. means for calculating the overall resistance of the neutral wire by multiplying the impedance by the cosine of the phase difference;

d. means for calculating the unit resistance by dividing the length of the neutral wire between the first point and the second point by a predetermined unit length and multiplying the quotient by the overall resistance; and e. means for generating the data output based on the unit resistance.

* * * * *